(12) United States Patent
Hauschild et al.

(10) Patent No.: US 6,802,846 B2
(45) Date of Patent: Oct. 12, 2004

(54) FOREIGN BODY RETRIEVAL DEVICE AND METHOD

(75) Inventors: Sidney F. Hauschild, Brooklyn Park, MN (US); Stephen L. Bolea, Watertown, MN (US); Johann J. Neisz, Coon Rapids, MN (US); Jeffrey A. Lechner-Riehle, Burnsville, MN (US); Robert C. Grant, New Hope, MN (US); Mark Polyak, Minnetonka, MN (US)

(73) Assignee: AMS Research Corporation, Minnetonka, MN (US)

(*) Notice: Subject to any disclaimer, the term of this patent is extended or adjusted under 35 U.S.C. 154(b) by 228 days.

(21) Appl. No.: 10/075,031

(22) Filed: Feb. 12, 2002

(65) Prior Publication Data

US 2002/0120277 A1 Aug. 29, 2002

Related U.S. Application Data

(60) Provisional application No. 60/268,194, filed on Feb. 12, 2001.

(51) Int. Cl.[7] .............................................. A61B 17/28
(52) U.S. Cl. .................................................... 606/110
(58) Field of Search ........................ 606/110, 113–115, 606/127, 128, 159, 200, 205, 206; 623/1.11; 600/101, 104, 116, 121, 153, 154

(56) References Cited

U.S. PATENT DOCUMENTS

| | | | |
|---|---|---|---|
| 4,865,030 A | | 9/1989 | Polyak |
| 5,156,609 A | * | 10/1992 | Nakao et al. ............... 606/142 |
| 5,224,954 A | * | 7/1993 | Watts et al. ................. 606/205 |
| 5,411,507 A | | 5/1995 | Heckele |
| 5,868,753 A | | 2/1999 | Schatz |
| 6,027,508 A | | 2/2000 | Ren et al. |
| 6,027,509 A | | 2/2000 | Schatz et al. |
| 6,090,129 A | * | 7/2000 | Ouchi ......................... 606/206 |
| 6,093,196 A | * | 7/2000 | Okada ......................... 606/127 |
| 6,159,219 A | | 12/2000 | Ren |
| 6,187,016 B1 | | 2/2001 | Hedges et al. |
| 6,302,895 B1 | | 10/2001 | Gobron et al. |
| 6,306,163 B1 | * | 10/2001 | Fitz ............................. 623/1.12 |
| 6,312,458 B1 | | 11/2001 | Golds |
| 6,348,056 B1 | | 2/2002 | Bates et al. |
| 6,348,060 B1 | | 2/2002 | Brown |
| 6,350,277 B1 | | 2/2002 | Kocur |
| 6,352,503 B1 | * | 3/2002 | Matsui et al. ............... 600/104 |
| 6,352,547 B1 | | 3/2002 | Brown et al. |
| 6,360,577 B2 | | 3/2002 | Austin |
| 6,361,540 B1 | * | 3/2002 | Gauderer et al. ........... 606/106 |
| 6,368,328 B1 | | 4/2002 | Chu et al. |
| 6,380,457 B1 | | 4/2002 | Yurek et al. |
| 6,383,196 B1 | | 5/2002 | Leslie et al. |
| 6,387,117 B1 | | 5/2002 | Arnold, Jr. et al. |
| 6,387,118 B1 | | 5/2002 | Hanson |
| 6,391,032 B2 | | 5/2002 | Blaeser et al. |
| 6,391,050 B1 | | 5/2002 | Broome |
| 6,391,051 B2 | | 5/2002 | Sullivan, III et al. |
| 6,395,008 B1 | | 5/2002 | Ellis et al. |
| 6,416,536 B1 | | 7/2002 | Yee |
| 6,605,104 B2 | * | 8/2003 | Sato et al. ................... 606/206 |
| 6,679,893 B1 | * | 1/2004 | Tran ............................ 606/127 |
| 2002/0035774 A1 | | 3/2002 | Austin |
| 2002/0087186 A1 | | 7/2002 | Shelso |
| 2002/0111666 A1 | | 8/2002 | Hart et al. |

FOREIGN PATENT DOCUMENTS

EP        0 829 242 A1    8/1996

* cited by examiner

*Primary Examiner*—Kevin Shaver
*Assistant Examiner*—Michael B. Priddy

(57) ABSTRACT

A foreign body retrieval device is disclosed. The device moves between an open position for receiving the foreign body and a closed position for capturing the foreign body. A novel method for retrieving a foreign body such as a stent is also disclosed.

14 Claims, 12 Drawing Sheets

FOREIGN BODY RETRIEVAL DEVICE AND METHOD

CROSS REFERENCE TO RELATED APPLICATIONS

The present application claims priority of U.S. Provisional Application Ser. No. 60/268,194, filed Feb. 12, 2001, the contents of which are fully incorporated herein by reference.

BACKGROUND

Many surgical procedures result in a foreign body being removed from a patient. In some instances, the foreign body is inadvertently dropped or misplaced in the body by a medical professional. In other instances, the foreign body the foreign body needs to be removed due to the presence of infection or likelihood that it will spread.

Implantable objects require removal for a variety of reasons including wear, rejection by the patient or infection. Stents are commonly inserted for a variety of medical reasons such as the prevention of tubular passage occlusions. Stents may be self-expanding or they may be expanded by other influences such as a balloon expander.

One example of a stent procedure is the implantation of a Urolume endoprosthesis to treat a urinary tract disorder such as benign prostatic hyperplasia (BPH), a urethral stricture (e.g. a bulbar urethral stricture) or detrusor external sphincter dyssynergis (DESD). It is believed that approximately 35 million men over the age of 50 suffer from BPH or other disorders potentially treatable by a stent procedure. While complications associated with a stent procedure are rare, it is sometimes desirable to remove an in vivo stent.

The removal of a wire stent from the urethra of a patient is a tedious and time consuming procedure. A foreign body extractor or alligator clip is typically used to grasp one region of the stent. Such devices may grasp only a single region of the stent at one time. Once the stent is grasped, the apparatus then can be used to pull the stent from the tissue. Some wire stents are woven or braided from independent wires. It is sometimes required to remove such a stent in a wire by wire fashion, particularly when there is substantial tissue ingrowth.

Other stent retrieval devices are used in cardiac and other surgical procedures. U.S. Pat. Nos. 5,411,507; 5,868,753; 6,027,508 6,027,509; 6,159,219; and 6,187,016 describe various stent retrieval devices.

BRIEF SUMMARY

The present invention comprises a foreign body retrieval apparatus having a handle, and an axially elongate member having a foreign body capturing assembly. The elongate member has an inner lumen that is sized and shaped to receive a viewing apparatus.

The apparatus also includes a substantially tubular member with an inner lumen that is sized and shaped to receive the elongate member. The handle, elongate member and tubular member are operatively associated with each other to move between i) an open position with the foreign body capturing assembly capable of receiving a foreign body, and ii) a closed position with the foreign body capturing assembly capable of controlling the foreign body.

The apparatus also includes a sheath having an inner lumen that is sized and shaped to afford sliding passage of the tubular member and the elongate member while in the closed position.

Preferably, the sheath is substantially cylindrical. In one embodiment, the outer diameter and length are sized and shaped to afford transurethral passage of the sheath from the external meatus of the urethra to the bladder of a male patient.

In one embodiment, the foreign body capturing assembly comprises a plurality of tines. Each tine has an inclined portion and a foreign body engagement portion. Preferably, the tines are constructed to be resiliently biased toward the open position. Preferably, the handle and tubular member are arranged so that movement toward the closed position causes the distal end of the tubular member to engage the inclined portions of the tines to cam the tines toward the closed position.

The foreign body extractor is particularly suitable for retrieving a stent, particularly a wire stent assembled from independent, nonattached wires. In one embodiment of the foreign body extractor, the foreign body engagement portions comprise hooks at distal ends of the tines situated so that the foreign body capturing assembly is capable of engaging a plurality of spaced regions of the stent substantially simultaneously. Preferably, each hook includes a concave surface that is sized and shaped to engage a wire of the stent.

In a preferred embodiment, the foreign body capturing assembly comprises three tines projecting about one hundred and twenty degrees relative to each other when viewed in a plane substantially perpendicular to the elongate axis of the elongate member, so that the stent may be grasped and collapsed in a substantially symmetrical fashion. More preferably, the hooks are substantially flat hooks situated at an angle that is substantially perpendicular to the elongate axis of the elongate member.

In addition to affording axial sliding motion of the elongate member and tubular member within the sheath, the lumen of the sheath also preferably is constructed to afford rotation of the elongate member and tubular member about the elongate axis of the elongate member.

Preferably, the handle and tubular member are arranged so that movement toward the closed position causes the distal end of the tubular member to engage the inclined portion of the tines to cam the tines toward the closed position, and in the open position, at least a portion of the tines and the foreign body engagement portions project radially beyond the outer diameter of the sheath.

When the foreign body comprises an in vivo wire stent having a radius (e.g. a self-expanding UroLume endoprosthesis), movement toward the closed position while the hooks are engaged with spaced wires on the stent preferably causes the stent to collapse radially so that relative axial movement between i) the tubular member, elongate member and engaged stent, and ii) the sheath results in removal of substantially all of the stent from the body.

In one embodiment, the handle comprises a thumb ring and a finger ring movable between adjacent and remote positions. The thumb ring is preferably assembled to be substantially stationary relative to the axially elongate member. In this embodiment, the finger ring is operatively associated with the tubular member so that movement of the finger member relative to the thumb ring from the remote toward the adjacent position moves the tubular member distally in a direction substantially parallel to the axis of the elongate member.

While the present invention is particularly suitable for retrieving stents, it is also noted that the device may also be used to capture a foreign body by surrounding or caging the foreign body (e.g. something within the bladder the should be removed). In the closed position, the distal ends of the arms are preferably substantially adjacent each other so that a foreign body may be captured by the arms and removed from the body through the sheath.

In another aspect, the present invention comprises a method of removing an in vivo stent. The method comprises the steps of: providing an assembly comprising a handle, and an axially elongate member having a stent capturing member, receiving at least a portion of the elongate member within a substantially tubular member, inserting a viewing apparatus into an inner lumen of the elongate member; receiving a portion of the tubular member within a sheath having a distal end; inserting the sheath into a tubular passage of a patient, viewing the in vivo stent with the viewing apparatus; moving the stent capturing member toward an open position with the handle, engaging the stent with the stent capturing member, then moving the stent capturing member toward a closed position, and causing relative axially movement between i) the tubular member and elongate member with the engaged stent, and ii) the distal end of the sheath to slide the stent from the patient.

Preferably, the step of causing relative axially movement between i) the tubular member and elongate member with the engaged stent, and ii) distal end of the sheath removes substantially all of the stent from the patient at once.

In one embodiment for treating a male, the step of inserting the sheath into a tubular passage of a patient includes the step of inserting the sheath from the external urethral meatus to a prostate region of a patient.

In another embodiment, the step of engaging the stent with the stent capturing member comprises the step of rotating the elongate member and tubular member about the axis of the elongate member while in the open position.

Preferably, the step of causing relative axially movement between i) the tubular member and elongate member with the engaged stent, and ii) distal end of the sheath to slide the stent from the patient includes the step of: applying traction to the tubular member and elongate member with the engaged stent and sliding the sheath distally relative to the handle.

The method may also include the step of resecting ingrown tissue away from the in vivo stent.

BRIEF DESCRIPTION OF THE DRAWING

Other features and advantages of the present invention will be seen as the following description of particular embodiments progresses in conjunction with the drawings, in which:

FIGS. 4 through 7 sequentially illustrate operation of an embodiment of foreign body extractor according to the present invention, wherein:

FIG. 4 illustrates the distal end portion of the assembly of FIG. 2 engaged with a stent and in the open position;

FIG. 5 illustrates the assembly moved toward a closed position;

FIG. 6 illustrates the tubular member and attached stent axially moved within the sheath of the assembly; and FIG. 7 illustrates the stent substantially captured within the sheath;

FIGS. 8 through 12 sequentially illustrate the removal of a stent wherein:

FIG. 8 is a simulation of the view through a viewing apparatus of a recently implanted stent;

FIG. 9 illustrates stent engaging hooks in a closed position and being advanced into an inner lumen of the stent;

FIG. 10 illustrates the hooks of FIG. 9 after being moved toward an open position and after being engaged with symmetrically spaced regions of the stent;

FIG. 11 illustrates the hooks of FIG. 10 after initially being moved from the open position back toward the closed position; and FIG. 12 illustrates the hooks and the engaged stent being moved more toward the closed position;

DETAILED DESCRIPTION

Figure 1:
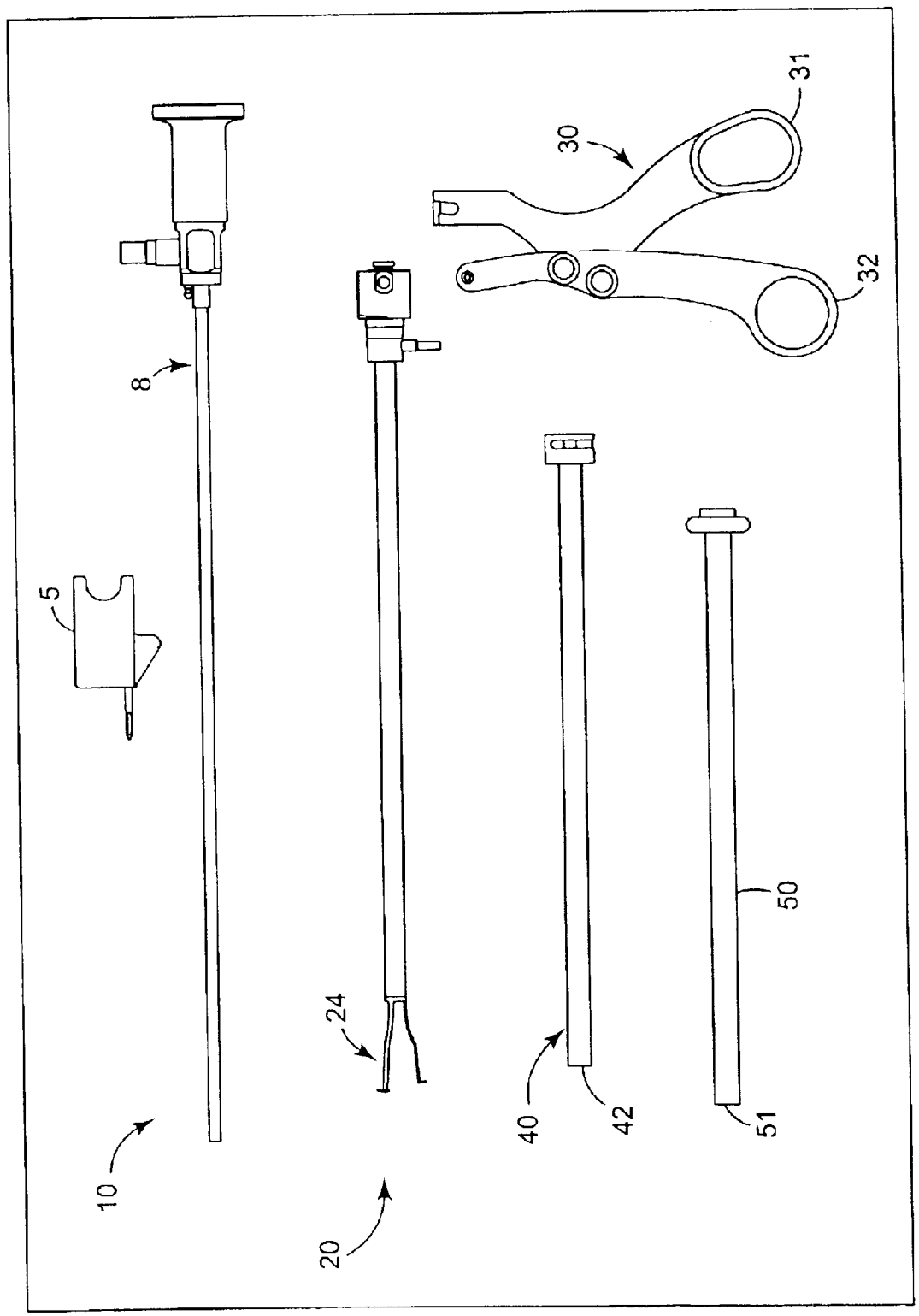
FIG. 1 is a side view of components of one embodiment of foreign body extraction assembly according to the present invention, with the elements disassembled to illustrate details.

The following description is meant to be illustrative only and not limiting. Other embodiments of this invention will be apparent to those of ordinary skill in the art in view of this description.

FIGS. 1 through 7 illustrate a first embodiment of a foreign body retrieval apparatus 10 according to the present invention. The apparatus 10 has a handle 30, and an axially elongate member 20 having a foreign body capturing assembly 24. The elongate member 20 has an inner lumen that is sized and shaped to receive a viewing apparatus 8. For example, the viewing apparatus may comprise any suitable scope such as those provided by Storz, Wolf, Olympus or ACMI.

The apparatus 10 also includes a substantially tubular member 40 with an inner lumen that is sized and shaped to receive the elongate member 20.

The handle 30, elongate member 20 and tubular member 40 are operatively associated with each other to move between i) an open position (FIG. 2) with the foreign body capturing assembly capable of receiving a foreign body, and ii) a closed position (e.g. FIG. 5) with the foreign body capturing assembly capable of controlling, manipulating and/or holding the foreign body (shown here as a stent 2).

Figure 5:
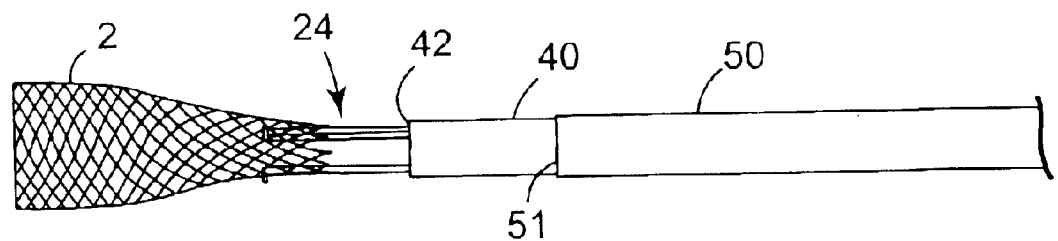

The apparatus also includes a sheath 50 having an inner lumen that is sized and shaped to afford sliding passage of the tubular member 40 and the elongate member 20 while in the closed position (FIG. 5). In addition to affording axial sliding motion of the elongate member 20 and tubular member 40 within the sheath 50, the lumen of the sheath 50 also is constructed to afford rotation of the elongate member and tubular member about the elongate axis of the elongate member 20.

Preferably, the sheath is substantially cylindrical. As an example not intended to be limiting, the outer diameter of the sheath may be between about 20 and 40 French, more preferably between about 24 and 28 French.

Preferably, the assembly 10 affords transurethral passage from the external meatus of the urethra to the bladder of a male patient. As an example, not intended to be limiting, the tubular member 40 may have an overall axial length between about 6 and 10 inches, more preferably between about 7 and 9 inches, and even more preferably about 8.7 inches. Additionally, the foreign body capturing assembly 24 preferably has a length between about 0.75 and 2 inches, more preferably between about 1 and 1.5 inches, and even more preferably about 1.3 inches.

Figure 3:
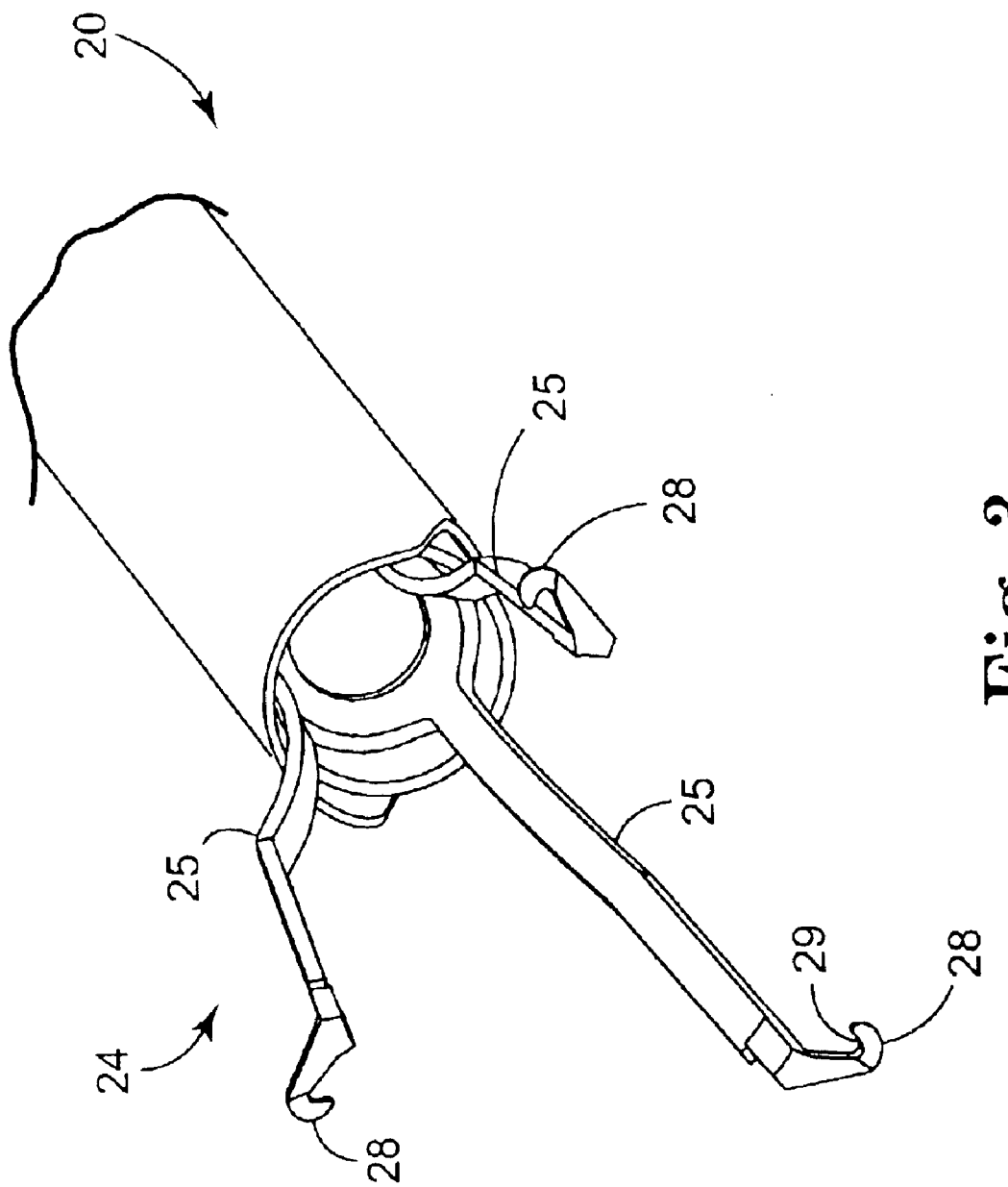
FIG. 3 is an exploded distal end view of an elongate member of FIG. 1.

FIG. 3 illustrates a foreign body capturing assembly 24 comprises a plurality of tines. Each tine has an inclined portion 25 and a foreign body engagement portion 29. Preferably, the tines are constructed to be resiliently biased toward the open position. For example, the tines may be constructed from MP35N stainless steel, available from Carpenter steel of California. For example, the tines may be constructed using an EDM process.

Preferably, the handle 30 and tubular member 40 are arranged so that movement toward the closed position causes the distal end 41 of the tubular member 40 to engage the inclined portions 25 of the tines to cam the tines toward the closed position.

The foreign body extractor shown in FIG. 3 is particularly suitable for retrieving a stent, particularly a wire stent assembled from independent, nonattached wires such as a UroLume endoprosthesis. The foreign body engagement portions 28 comprise hooks at distal ends of the tines situated so that the foreign body capturing assembly is capable of engaging a plurality of spaced regions of the stent substantially simultaneously (e.g. see FIG. 4). Preferably, each hook includes a concave surface 29 that is sized and shaped to engage a wire of the stent. Opposite the concave surface 29 is a convex surface. The convex surface can be slightly sharp (e.g. not completely blunt) to afford passage through tissue (e.g. prostatic urethral tissue) that might be ingrown into the holes of the stent.

The foreign body capturing assembly shown in FIG. 3 comprises three tines projecting about one hundred and twenty degrees relative to each other when viewed in a plane substantially perpendicular to the elongate axis of the elongate member 20. The symmetrical arrangement allows the stent to be grasped and collapsed at multiple, spaced apart points in a substantially symmetrical fashion. The hooks 28 are substantially flat hooks preferably situated at an angle that is substantially perpendicular to the elongate axis of the elongate member 20. Angles other than perpendicular are also within the scope of the present invention.

Figure 4:
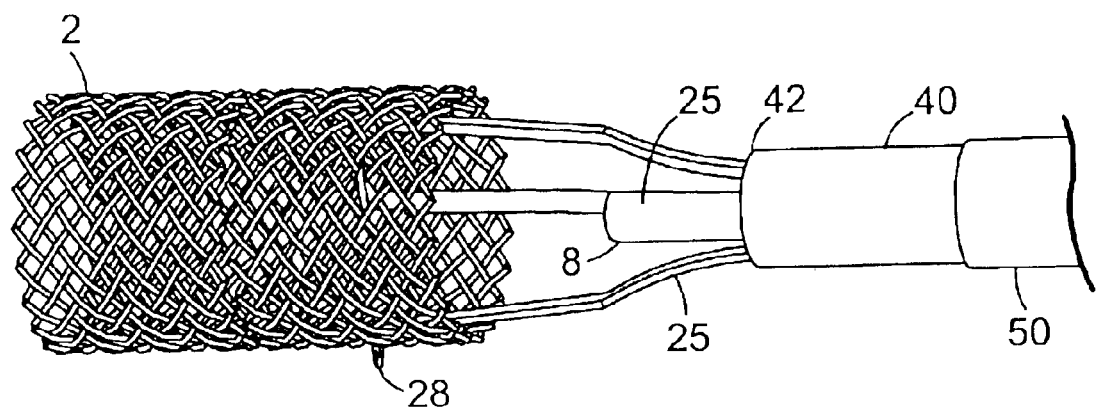

FIGS. 4 through 7 sequentially illustrate operation of the foreign body extractor 10. FIG. 4 illustrates the foreign body engagement assembly engaged with a stent 2. To get to this point, the apparatus 10 may be placed in the closed position, threaded through the sheath 50 and moved a predetermined distance within the lumen of the stent 2 (e.g. four diamonds from the end of the stent 2) and then moved to the open position. Once the apparatus is moved to the open position, the elongate member 20 and tubular member 40 may be rotated (e.g. clockwise or counterclockwise depending on the orientation of the hooks 28) within sheath 50 until the concave surfaces 29 of the hooks 28 engage wires of the stent 2.

FIG. 5 illustrates the apparatus 10 being moved toward a closed position. When the foreign body comprises an in vivo wire stent 2 having a radius (e.g. a self-expanding UroLume endoprosthesis), movement toward the closed position while the hooks 28 are engaged with spaced wires on the stent 2 preferably causes the stent 2 to collapse radially so that relative axial movement between i) the tubular member 40, elongate member 20 and engaged stent 2, and ii) the sheath 50 results in removal of substantially all of the stent from the body. This affords the advantage of removing the entire stent at once without the need to independently locating, grasping and removing individual wires of the stent.

Figure 6:
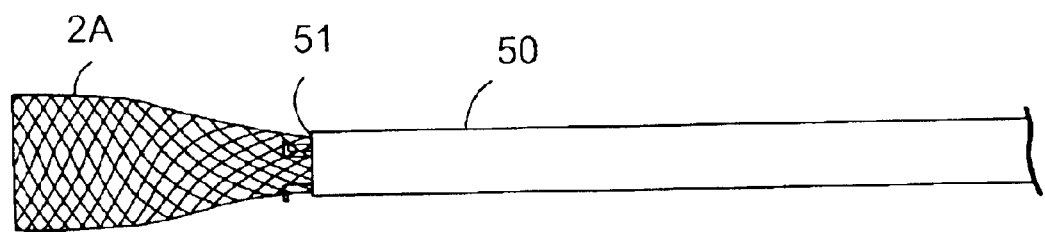
Figure 7:
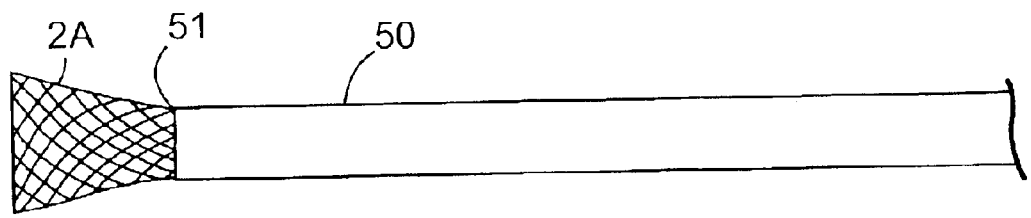

The apparatus 10 preferably collapses the diameter of the stent 2 so that it fits within the inner lumen of sheath 50. FIG. 6 illustrates the arrangement of components after the tubular member 30 and a portion of the stent 2 attached to elongate member 20 are axially moved within the inner lumen of the sheath 50. FIG. 7 illustrates the stent 2 substantially captured within the distal end 51 of the sheath 50.

The handle 30 and tubular member 40 are arranged so that movement toward the closed position causes the distal end 42 of the tubular member 40 to engage the inclined portions 25 of the tines to cam the tines toward the closed position. In the open position, at least a portion of the tines and the foreign body engagement portions 24 project radially beyond the outer diameter of the sheath 50 (e.g. see FIG. 4). This affords an initial approach of the stent 2 from the inner surfaces of the stent and subsequent radial expansion of the hooks 28 so that the convex portions of the hooks 28 extend outside the outer surface of the stent 2.

It should be noted that a plurality of different handle types are within the scope of the present invention. Any suitable connecting linkage between the handle 30 and tubular member 40 may be used, such as a pin and slot linkage. Also, the handle may include operative elements other than thumb and finger rings, such as movable levers or other manipulable elements.

Figure 2:
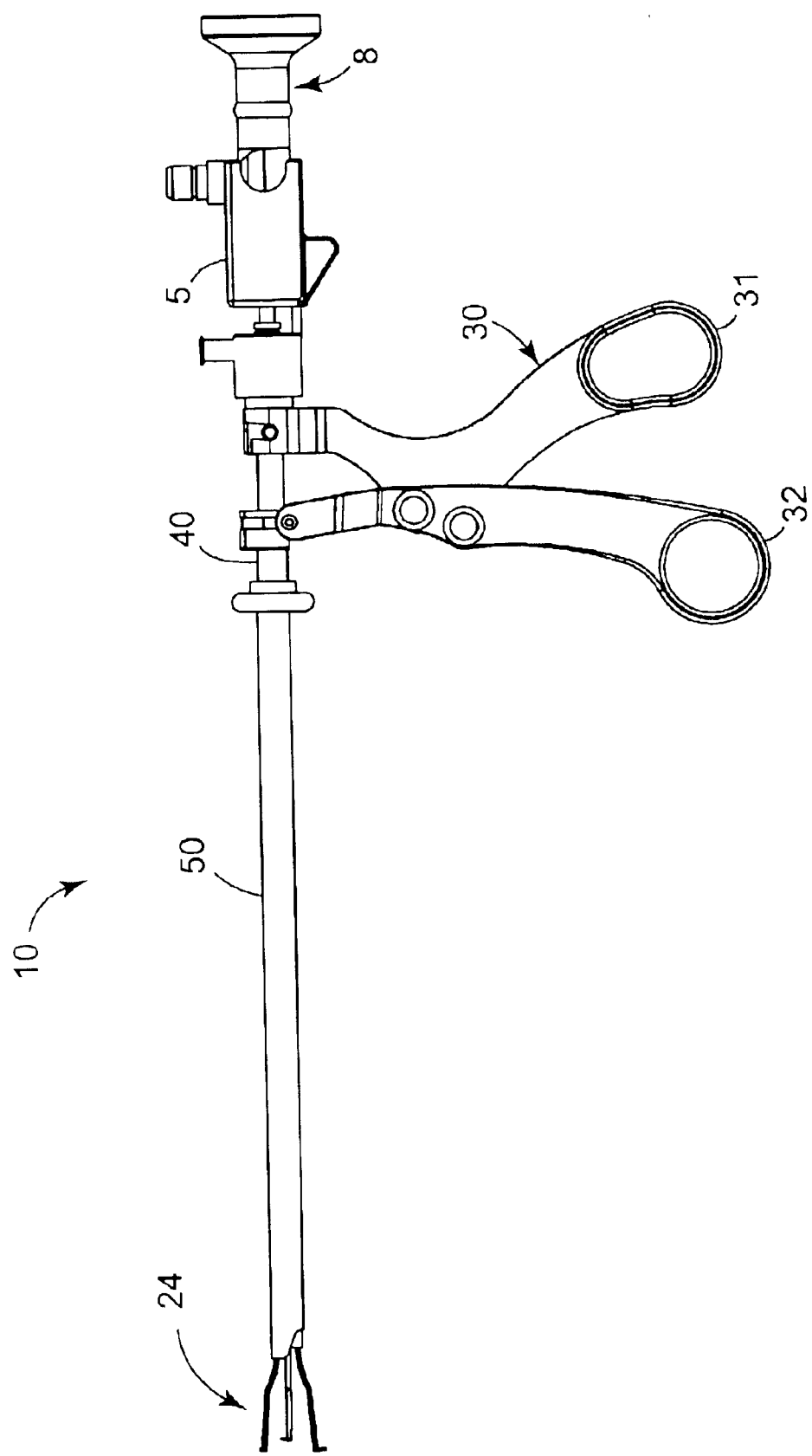
FIG. 2 is a side view of the elements of FIG. 2 shown in an assembled condition and in an open position.

In FIGS. 1–3, the handle 30 comprises a thumb ring 31 and a finger ring 32 movable between adjacent and remote (see FIG. 2) positions. To move the handle 30 to the adjacent position (and close the apparatus 10), the finger ring 32 may be moved in the direction of the arrow in FIG. 2 toward the thumb ring 31.

The thumb ring 31 is preferably assembled to be substantially stationary relative to the axially elongate member 24. The finger ring 32 is operatively associated with the tubular member 40 so that movement of the finger ring 32 relative to the thumb ring 31 from the remote (FIG. 2) toward the adjacent position (in the direction of the arrow of FIG. 2) moves the tubular member 40 distally in a direction substantially parallel to the axis of the elongate member 20.

Figure 13:
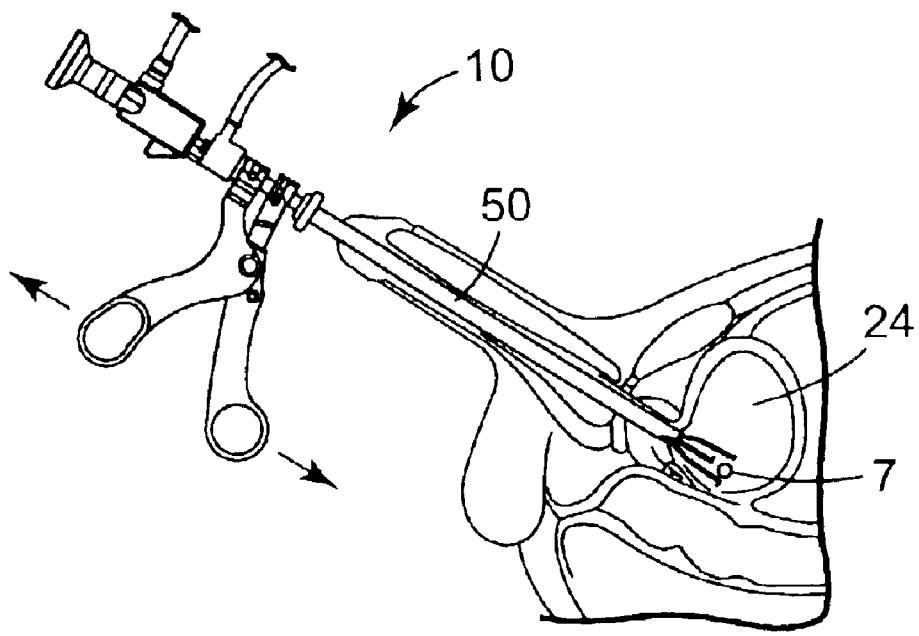
FIG. 13 is a side view of an apparatus being used on a male patient to approach a foreign body in the bladder.
Figure 14:
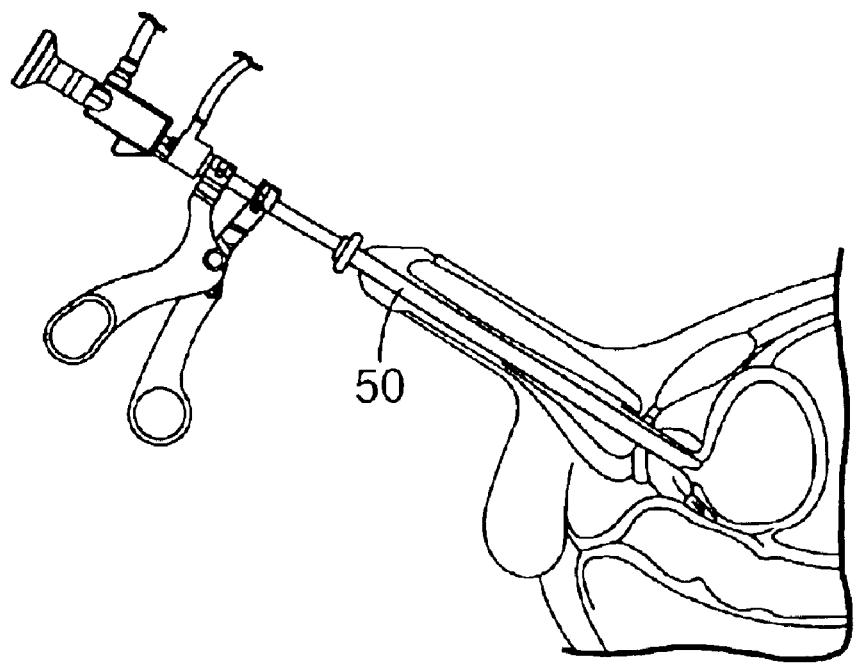
FIG. 14 is a side view of the apparatus of FIG. 13 after the foreign body is captured between the tines and moved within the sheath.

While the present invention is particularly suitable for retrieving stents, it is also noted that the device may also be used to capture a foreign body by surrounding or caging the foreign body (e.g. something within the bladder the should be removed). FIG. 13 is a side view of an apparatus being used on a male patient to approach a foreign body 7 in the bladder. FIG. 14 is a side view of the apparatus of FIG. 13 after the foreign body 7 was captured between the arm and moved within the sheath 50. In the closed position, the distal ends of the arms are preferably substantially adjacent each other so that a foreign body may be captured or caged by the arms and removed from the bladder through the sheath 50.

Figure 15:
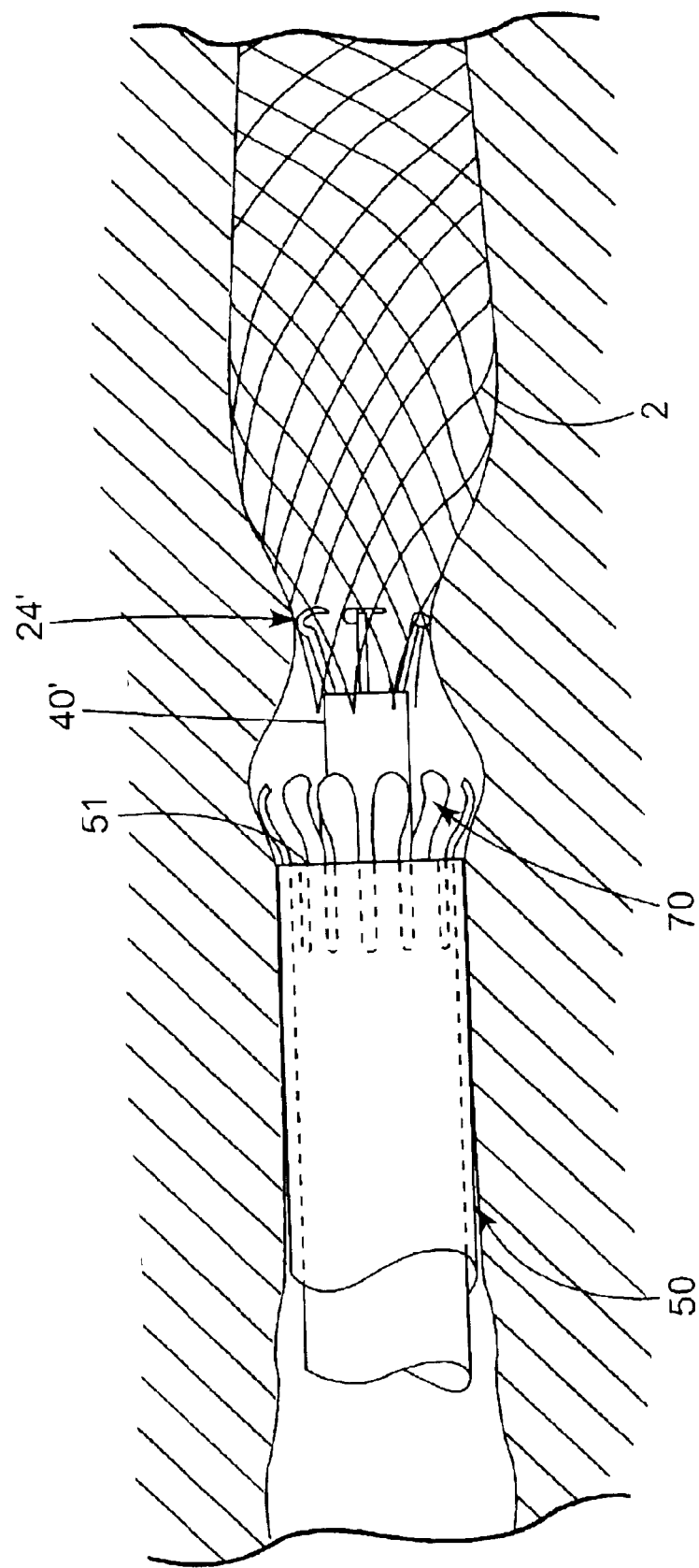
FIG. 15 is a side view of an alternate embodiment of apparatus according to the present invention.

FIG. 15 illustrates another embodiment of apparatus according to the present invention. The embodiment shown in FIG. 15 includes a tissue expander 70 to reduce the chance that tissue could block removal of the foreign body.

The apparatus 10 may be provided as a kit or as separable components. 11. For example, the kit may optionally include a viewing apparatus stabilizer 5 (see FIG. 1).

The apparatus 10 may be entirely or partially reusable, or disposable. Components thereof may also be either reusable or disposable. The apparatus 10 or components thereof may be sterilizable through any suitable techniques such as ethylene oxide, steam, plasma or liquid or vapor chemical sterilization reactants (e.g. hydrogen peroxide or peracetic acid). Optionally, the apparatus 10 may be constructed to be single use only.

EXAMPLES OF METHODS

Many methods are contemplated herein. Although the methods of use as disclosed herein generally relate to urinary conditions and treatments/procedures, other conditions and treatments/procedures such are cardiac stent removal procedures are also included within the scope of the present invention. Procedures that address problems other than stent removal are also contemplated alone or in conjunction with the present invention. Further, the term "urethra" is used for brevity and reader convenience. As such, removal of foreign bodies from the "urethra," "bladder", "prostate" and "bladder neck" are also included within the scope of the present invention.

FIGS. 8–12 sequentially illustrate the removal of a stent. The method comprises the steps of: providing an assembly comprising a handle, and an axially elongate member having a stent capturing member, receiving at least a portion of the elongate member within a substantially tubular member, inserting a viewing apparatus into an inner lumen of the elongate member; receiving a portion of the tubular member within a sheath having a distal end; inserting the sheath into a tubular passage of a patient, viewing the in vivo stent with the viewing apparatus; moving the stent capturing member toward an open position with the handle, engaging the stent with the stent capturing member, then moving the stent capturing member toward a closed position, and causing relative axially movement between i) the tubular member and elongate member with the engaged stent, and ii) the distal end of the sheath to slide the stent from the patient.

Figure 8:
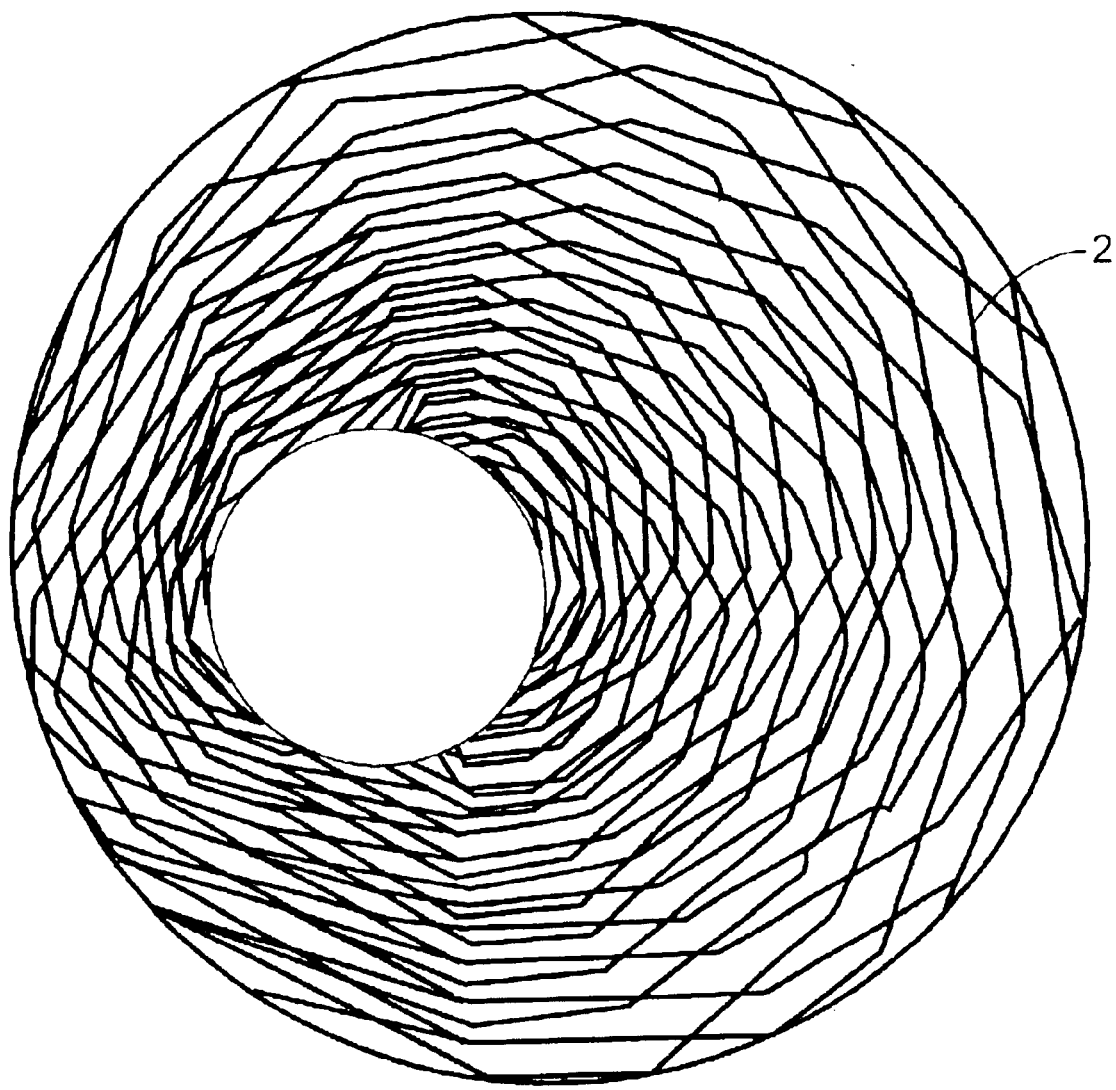
Figure 9:
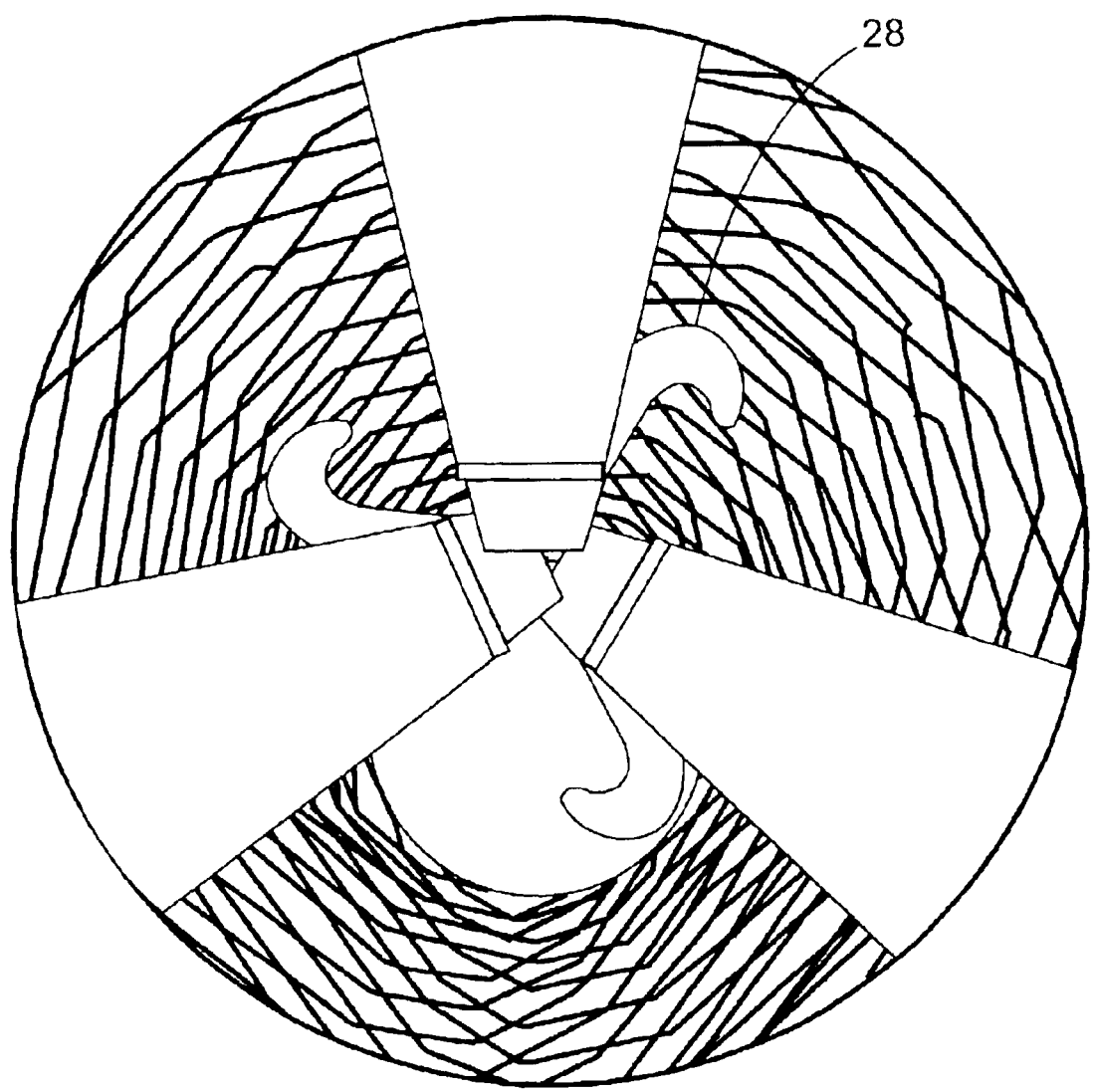
Figure 10:
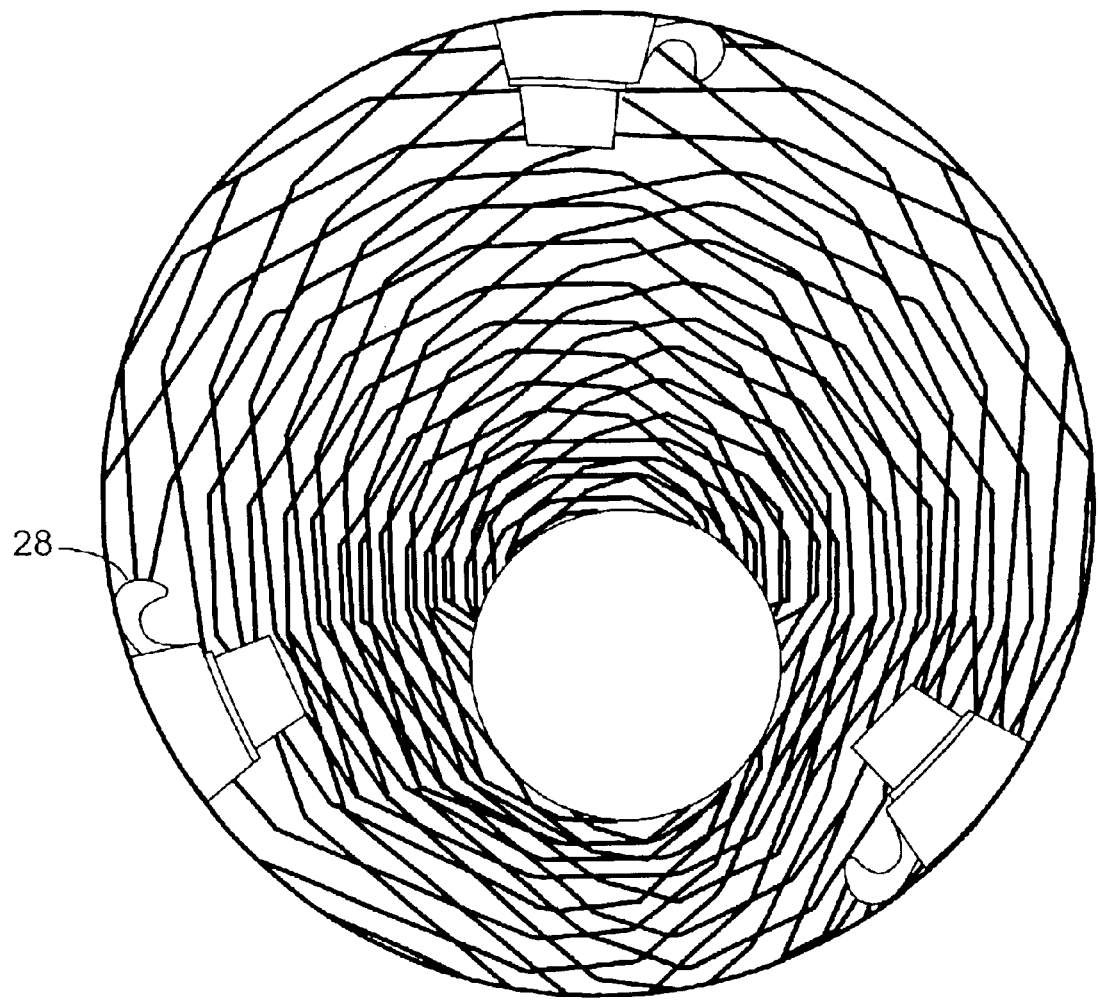
Figure 11:
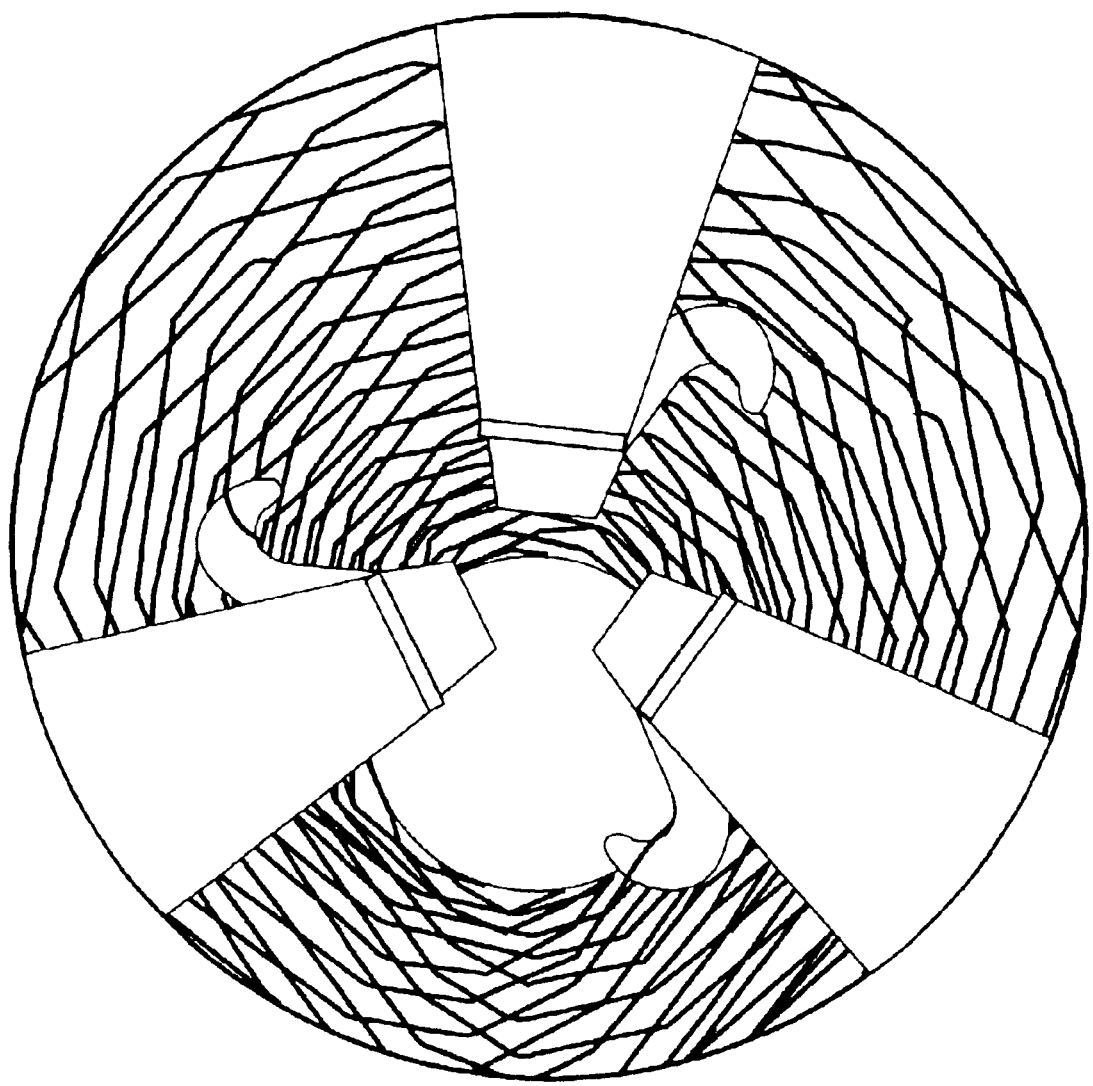
Figure 12:
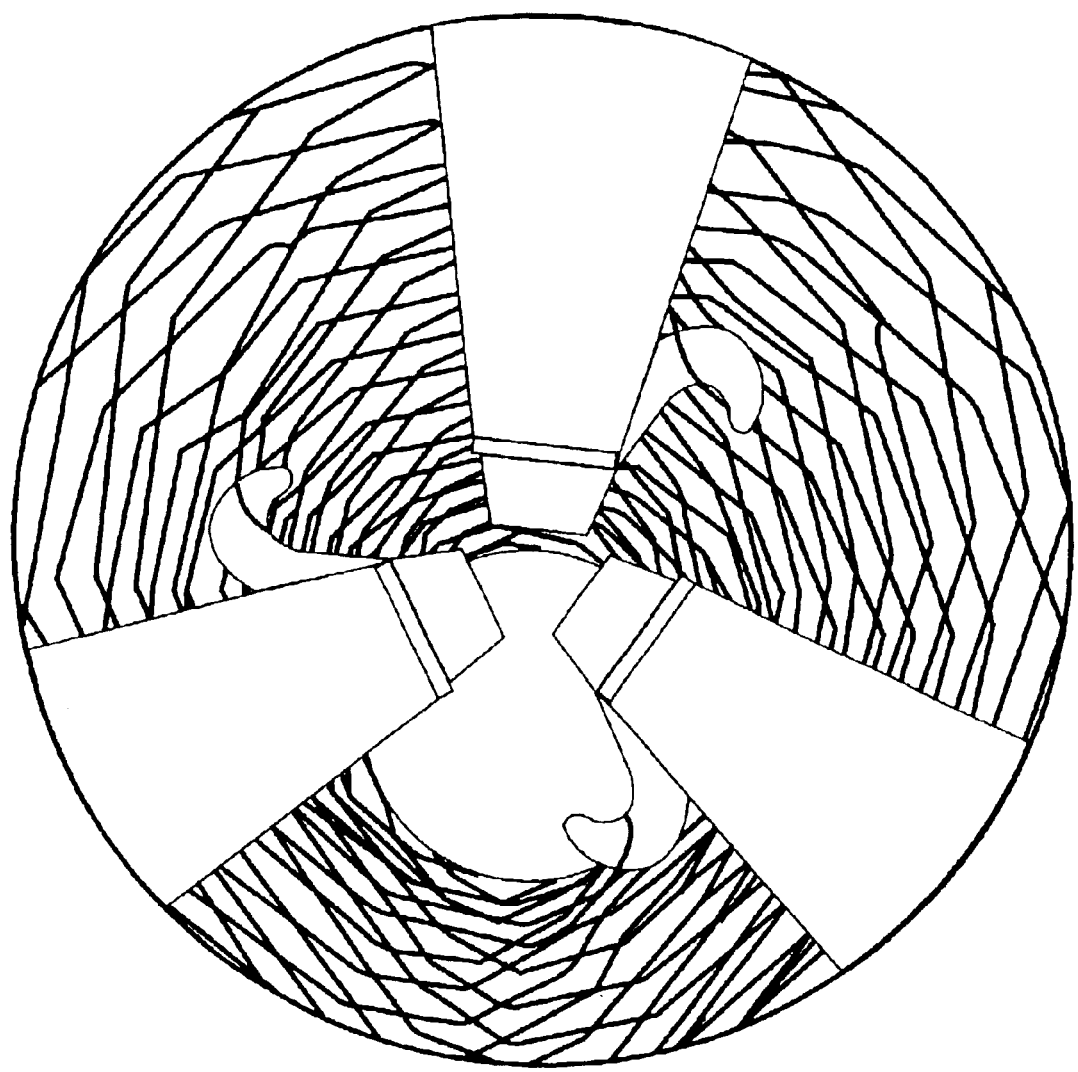

FIG. 8 is a simulation of the view through a viewing apparatus of a recently implanted stent. FIG. 9 illustrates stent engaging hooks in a closed position and being advanced into an inner lumen of the stent. FIG. 10 illustrates the hooks of FIG. 9 after being moved toward an open position and after being engaged with symmetrically spaced regions of the stent. FIG. 11 illustrates the hooks of FIG. 10 after initially being moved from the open position back toward the closed position. FIG. 12 illustrates the hooks and the engaged stent being moved more toward the closed position.

Preferably, the step of causing relative axially movement between i) the tubular member and elongate member with the engaged stent, and ii) distal end of the sheath removes substantially all of the stent from the patient at once.

In one embodiment for treating a male, the step of inserting the sheath into a tubular passage of a patient includes the step of inserting the sheath from the external urethral meatus to a prostate region of a patient.

In another embodiment, the step of engaging the stent with the stent capturing member comprises the step of rotating the elongate member and tubular member about the axis of the elongate member while in the open position.

Preferably, the step of causing relative axially movement between i) the tubular member and elongate member with the engaged stent, and ii) distal end of the sheath to slide the stent from the patient includes the step of: applying traction to the tubular member and elongate member with the engaged stent and sliding the sheath distally relative to the handle.

The method may also include the step of resecting ingrown tissue away from the in vivo stent.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A foreign body retrieval apparatus comprising:

a handle, an axially elongate member having a foreign body capturing assembly, the elongate member having an inner lumen that is sized and shaped to receive a viewing apparatus;

a substantially tubular member having a distal end and an inner lumen that is sized and shaped to receive the elongate member;

the handle, elongate member and tubular member being operatively associated to move between an open position with the foreign body capturing assembly adapted to receive the foreign body, and a closed position with the foreign body capturing assembly adapted to control the foreign body, and a sheath having an inner lumen that is sized and shaped to afford sliding passage of the tubular member and the elongate member while in the closed position.

2. A foreign body retrieval apparatus according to claim 1 wherein the sheath is substantially cylindrical with an outer diameter and a length, and the outer diameter and length are sized and shaped to afford transurethral passage of the sheath from the external meatus of the urethra to the bladder of a male patient.

3. A foreign body retrieval apparatus according to claim 1 wherein the foreign body capturing assembly comprises a plurality of tines, each tine having an inclined portion and a foreign body engagement portion, each tine being constructed to be resiliently biased toward the open position, and the handle and tubular member being arranged so that movement toward the closed position causes the distal end of the tubular member to engage the inclined portions of the tines to cam the tines toward the closed position.

4. A foreign body retrieval apparatus comprising:

a handle, an axially elongate member having a foreign body capturing assembly, the elongate member having an inner lumen that is sized and shaped to receive a viewing apparatus;

a substantially tubular member having a distal end and an inner lumen that is sized and shaped to receive the elongate member;

the handle, elongate member and tubular member being operatively associated to move between an open position with the foreign body capturing assembly adapted to receive the foreign body, and a closed position with the foreign body capturing assembly adapted to control the foreign body, a sheath having an inner lumen that is sized and shaped to afford sliding passage of the tubular member and the elongate member while in the closed position, wherein the foreign body capturing assembly comprises a plurality of tines, each tine having an inclined portion and a foreign body engagement portion, each tine being constructed to be resiliently biased toward the open position, the handle and tubular member being arranged so that movement toward the closed position causes the distal end of the tubular member to engage the inclined portions of the tines to cam the tines toward the closed position, and wherein the foreign body comprises a stent and the foreign body engagement portions comprise hooks at distal ends of the tines situated so that the foreign body capturing assembly is capable of engaging a plurality of spaced regions of the stent substantially simultaneously.

5. A foreign body retrieval apparatus according to claim 4 wherein the stent is a wire stent and each hook includes a concave surface that is sized and shaped to engage a wire of the stent.

6. A foreign body retrieval apparatus according to claim 5 wherein the plurality of tines comprises three tines projecting about one hundred and twenty degrees relative to each other when viewed in a plane substantially perpendicular to the elongate axis of the elongate member, so that the stent may be grasped and collapsed in a substantially symmetrical fashion.

7. A foreign body retrieval apparatus according to claim 4 wherein the hooks are substantially flat hooks situated at an angle that is substantially perpendicular to the elongate axis of the elongate member.

8. A foreign body retrieval apparatus according to claim 1 wherein the sheath is substantially cylindrical with an outer diameter and the lumen of the sheath is constructed to afford rotation of the elongate member and tubular member about the elongate axis of the elongate member.

9. A foreign body retrieval apparatus according to claim 8 wherein the foreign body capturing assembly comprises a plurality of tines, each tine having an inclined portion and a foreign body engagement portion, each tine being constructed to be resiliently biased toward the open position, and the handle and tubular member being arranged so that movement toward the closed position causes the distal end of the tubular member to engage the inclined portion of the tines to cam the tines toward the closed position, and in the open position, at least a portion of the tines and the foreign body engagement portions project radially beyond the outer diameter of the sheath.

10. A foreign body retrieval apparatus comprising:

a handle, an axially elongate member having a foreign body capturing assembly, the elongate member having an inner lumen that is sized and shaped to receive a viewing apparatus;

a substantially tubular member having a distal end and an inner lumen that is sized and shaped to receive the elongate member;

the handle, elongate member and tubular member being operatively associated to move between an open position with the foreign body capturing assembly adapted to receive the foreign body, and a closed position with the foreign body capturing assembly adapted to control the foreign body, a sheath having an inner lumen that is sized and shaped to afford sliding passage of the tubular member and the elongate member while in the closed position, wherein the sheath is substantially cylindrical with an outer diameter and the lumen of the sheath is constructed to afford rotation of the elongate member and tubular member about the elongate axis of the elongate member, wherein the foreign body capturing assembly comprises a plurality of tines, each tine having an inclined portion and a foreign body engagement portion, each tine being constructed to be resiliently biased toward the open position, the handle and tubular member being arranged so that movement toward the closed position causes the distal end of the tubular member to engage the inclined portion of the tines to cam the tines toward the closed position, in the open position, at least a portion of the tines and the foreign body engagement portions project radially beyond the outer diameter of the sheath, wherein the foreign body comprises an in vivo wire stent having a radius, the foreign body engagement portion comprises hooks having concave portions sized and shaped to engage a wire of the stent, and movement toward the closed position while the hooks are engaged with the wires of the stent causes the stent to collapse radially so that relative axial movement between i) the tubular member, elongate member and engaged stent, and ii) the sheath results in removal of substantially all of the stent.

11. A foreign body retrieval apparatus comprising:

a handle, an axially elongate member having a foreign body capturing assembly, the elongate member having an inner lumen that is sized and shaped to receive a viewing apparatus;

a substantially tubular member having a distal end and an inner lumen that is sized and shaped to receive the elongate member;

the handle, elongate member and tubular member being operatively associated to move between an open position with the foreign body capturing assembly adapted to receive the foreign body, and a closed position with the foreign body capturing assembly adapted to control the foreign body, a sheath having an inner lumen that is sized and shaped to afford sliding passage of the tubular member and the elongate member while in the closed position, and further comprising a tissue expander to reduce the chance that tissue may block removal of the foreign body.

12. A foreign body retrieval apparatus comprising:

a handle, an axially elongate member having a foreign body capturing assembly, the elongate member having an inner lumen that is sized and shaped to receive a viewing apparatus;

a substantially tubular member having a distal end and an inner lumen that is sized and shaped to receive the elongate member;

the handle, elongate member and tubular member being operatively associated to move between an open position with the foreign body capturing assembly adapted to receive the foreign body, and a closed position with the foreign body capturing assembly adapted to control the foreign body, a sheath having an inner lumen that is sized and shaped to afford sliding passage of the tubular member and the elongate member while in the closed position, and further comprising a viewing apparatus stabilizer.

13. A foreign body retrieval apparatus according to claim 1 wherein the handle comprises a thumb ring and a finger ring movable between adjacent and remote positions, the thumb ring assembled to be substantially stationary relative to the axially elongate member, the finger ring being operatively associated with the tubular member so that movement of the finger ring relative to the thumb ring from the remote toward the adjacent position moves the tubular member distally in a direction substantially parallel to the axis of the elongate member.

14. A foreign body retrieval apparatus comprising:

a handle, an axially elongate member having a foreign body capturing assembly, the elongate member having an inner lumen that is sized and shaped to receive a viewing apparatus;

a substantially tubular member having a distal end and an inner lumen that is sized and shaped to receive the elongate member;

the handle, elongate member and tubular member being operatively associated to move between an open position with the foreign body capturing assembly adapted to receive the foreign body, and a closed position with the foreign body capturing assembly adapted to control the foreign body, a sheath having an inner lumen that is sized and shaped to afford sliding passage of the tubular member and the elongate member while in the closed position, wherein the foreign body capturing assembly comprises at least three arms having distal ends, and wherein in the closed position, the distal ends of the arms are substantially adjacent each other so that a foreign body may be captured by the arms and removed through the sheath.

* * * * *